United States Patent
Stuiver et al.

(10) Patent No.: US 6,774,281 B1
(45) Date of Patent: Aug. 10, 2004

(54) METHOD FOR THE INDUCTION OF PATHOGEN RESISTANCE IN PLANTS

(75) Inventors: Maarten Hendrik Stuiver, Oegstgeest (NL); Jerôme Hubertina Henricus Victor Custers, Alphen a/d Rijn (NL); Lambertus Henricus Simons, Amstelveen (NL)

(73) Assignee: Syngenta Mogen BV, Leiden (NL)

( * ) Notice: Subject to any disclaimer, the term of this patent is extended or adjusted under 35 U.S.C. 154(b) by 0 days.

(21) Appl. No.: 09/623,551

(22) PCT Filed: Mar. 8, 1999

(86) PCT No.: PCT/EP99/01672

§ 371 (c)(1),
(2), (4) Date: Nov. 15, 2000

(87) PCT Pub. No.: WO99/45129

PCT Pub. Date: Sep. 10, 1999

(30) Foreign Application Priority Data

Mar. 6, 1998 (EP) .............................. 98104076

(51) Int. Cl.⁷ ...................... C12N 15/09; C12N 15/29; C12N 15/82; A01H 5/00
(52) U.S. Cl. .................. 800/279; 800/278; 800/298; 800/295; 800/306; 536/23.6; 536/24.1; 435/419; 435/468; 435/320.1
(58) Field of Search ................. 800/279, 278, 800/295, 306; 435/419, 468; 536/23.6, 24.1

(56) References Cited

FOREIGN PATENT DOCUMENTS

| WO | WO 91/15585 | 10/1991 |
|---|---|---|
| WO | WO 95/31564 | 10/1995 |
| WO | WO 96/22375 | 7/1996 |
| WO | WO 96/28561 | 9/1996 |
| WO | WO 96/34949 | 11/1996 |
| WO | WO 97/47183 | 12/1997 |
| WO | WO 97/49823 | 12/1997 |
| WO | WO 98/53073 | 11/1998 |

OTHER PUBLICATIONS

Ryals et al, "Systemic Acquired Resistance", 1996, The Plant Cell vol. 8, pp. 1809–1819.*
Broun et al, "Catalytic Plasticity of Fatty Acid Modification Enzymes Underlying Chemical Diversity of Plant Lipids", 1998, Science vol. 282, pp. 1315–1317.*
Lazar et al, "Transforming Growth Factor x:Mutation of Aspartic Acid 47 and Leucine 48 Results in Different Biological Activities", 1988, Molecular and Cellular Biology vol. 8 No. 3, pp. 1247–1252.*
Ronald, Pamela C., Plant Molecular Biology, vol. 35, pps. 179–186, 1997.
Century, Karen S., Thesis, Univ.of California, 1996.
Dietrich, Robert A., Cell, vol. 88, pps. 685–694, Mar. 7, 1997.
Century, Karen S., et al., Science, vol. 278, pps. 1963–1965, Dec. 12, 1997.
Dangl, Jeffery L., The Plant Cell, vol. 8, pps. 1793–1807, 1996.

* cited by examiner

Primary Examiner—Elizabeth F. McElwain
Assistant Examiner—Medina A. Ibrahim
(74) Attorney, Agent, or Firm—Gregory W. Warren

(57) ABSTRACT

The invention comprises a method for the induction of pathogen resistance in plants characterized by transforming a plant with a polynucleotide sequence comprising a pathogen inducible promoter which regulates the expression of a plant signal transduction protein or a homologue thereof which when constitutively expressed gives rise to a hypersensitive response in plants. Alternatively, the invention comprises a method for the induction of pathogen resistance in plants characterized by transforming a plant with a polynucleotide sequence comprising a pathogen inducible promoter which regulates the expression of a compound which is able to alleviate the inhibitory effect of a protein on the signal transduction pathway leading to a hypersensitive response in plants.

6 Claims, 1 Drawing Sheet

METHOD FOR THE INDUCTION OF PATHOGEN RESISTANCE IN PLANTS

Figure 1:
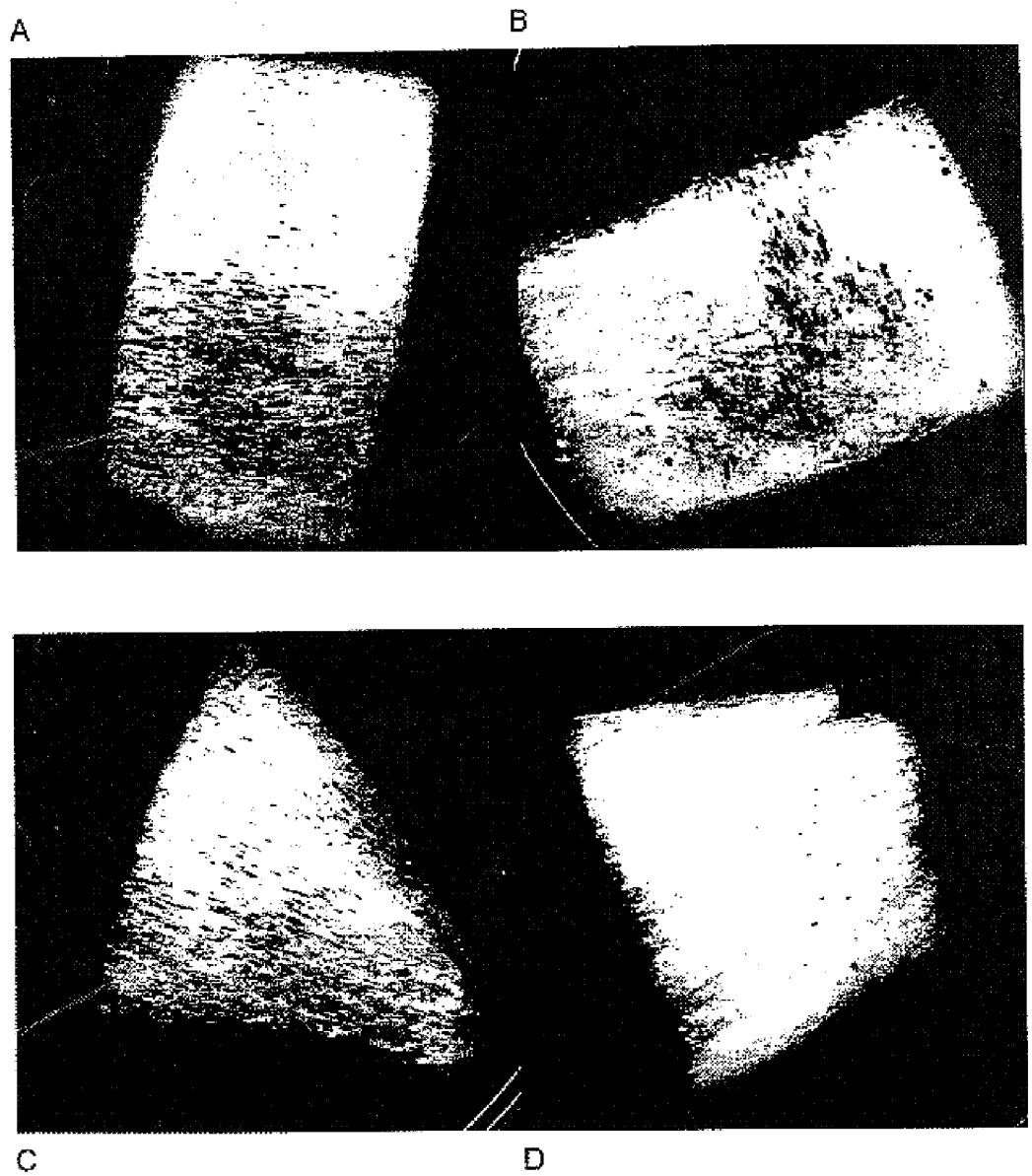

The present invention relates, inter alia, to recombinant polynucleotides, proteins and methods of imparting to and/ or enhancing an organisms ability to resist pathogens.

BACKGROUND

Plants resistant to pathogens often are found to evoke their resistance through a mechanism which eventually yields a hypersensitive response (HR) resulting in rapid cell death of the infected plant cells. This rapid cell death or necrosis inhibits the pathogen from further growth and thus stops the infection. This mechanism is known within the art (Klement, Z., In: Phytopathogenic Prokaryotes, Vol. 2, eds.: Mount, M. S. and Lacy, G. H., New York, Academic Press, 1982, pp. 149–177). The HR is often confused with other lesion-like phenomena, but a typical HR gives local cell death and is associated with secondary responses such as callus deposition, generation of active oxygen species, induction of phytoalexins, changes in ion fluxes across membranes and induction of acquired resistance (AR) (Hammond-Kosack, K. E., et al., Plant Physiol. 110, 1381–1394, 1996).

Pathogen resistance can be elicited by response to elicitor compounds, which are frequently found to be of proteinaceous nature (Arlat, M., et al., EMBO J., 13, 543–553, 1994; Baker, C. J. et al., Plant Physiol. 102, 1341–1344, 1993; Staskawicz, B. J. et al., Proc. Natl. Acad. Sci. USA 81, 6024–6028, 1984; Vivian, A. et al., Physiol. Mol. Plant Pathol. 35, 335–344, 1989; Keen, N. T., Ann. Rev. Gen. 24, 447–463, 1990; Ronald, P. C. et al., J. Bacteriol. 174, 1604–1611, 1992; Whithan, S. et al., Cell 78, 1–20, 1994; Kobe, B. and Deisenhofer, J., Trends Biochem. Sci. 19, 415, 1994; and Honée G. et al., Plant Mol. Biol. 29, 909–920, 1995). These elicitor proteins (encoded by avirulence genes) are thought to bind to a resistance protein available in the plant, therewith starting a cascade of events resulting in the HR. The elicitor proteins are characterized by the fact that they are race-specific and only are able to elicit the response with a corresponding (also specific) resistance protein. The concept of avirulence-gene based resistance is also known under the name of the gene-for-gene response. Avirulence genes have been cloned from bacterial pathogens (such as Pseudomonas and Xanthomonas) and from fungal pathogens (such as *Cladosporium fulvum, Rhynchosporium secalis* and *Phytophthora parasitica*). Also plant genes coding for some of the corresponding resistance genes have been cloned (such as the tomato gene Cf9 corresponding to the avirulence gene avr9 from *Cladosporium fulvum*, and the tomato Pto-gene corresponding to the avirulence gene avrPto from Pseudomonas).

It has recently become clear that the plant resistance proteins when activated by interaction with the pathogen-derived elicitor proteins are capable of inducing a signal transduction pathway. It has been established that some interactions at least partly use a common pathway (Century, K. S., et al., Science 278, 1963–1965, 1997). In this publication the NDR1 locus has been shown to be required for resistance to the bacterial pathogen *Pseudomonas syringae* pv. tomato and to the fungal pathogen *Peronospora parasitica*. Similarly Parker, J. E., et al. (The Plant Cell 8, 2033–2046, 1996) have shown that the product encoded by the eds1-locus in *Arabidopsis thaliana* also has a key function in the signal transduction pathway after infection with *Peronospora parasitica*, but not after infection with *Pseudomonas syringae* pv glycinae.

Recently a report has been published stating that also plant derived proteins can elicit cell-death like phenomena (Karrer, E. E. et al., Plant Mol. Biol. 36, 681–690, 1998). In this publication 11 clones have been described which were able to produce lesions in tobacco plants.

Methods to use resistance genes to confer pathogen resistance to plants are often hampered by the fact that the resistance is only limited to a few specific pathotypes.

Thus there is still need for a system which can convert a general pathogen resistance to plants which is silent when no pathogens are infecting.

SUMMARY OF THE INVENTION

The invention now concerns a method for the induction of pathogen resistance in plants characterized by transforming, a plant with a polynucleotide sequence comprising a pathogen inducible promoter which regulates the expression of a plant signal transduction protein or a homologue thereof which when expressed gives rise to a hypersensitive response in plants.

Specifically the signal transducing protein is ndr1 or a homologue thereof, eds1 or a homologue thereof, or Xa21 or a homologue thereof.

It is also possible that the signal transduction protein is selected from the group consisting of a G-protein, a protein kinase, an AMP-cyclase and a protein phosphatase. Another embodiment of this part of the invention is where the signal transduction protein is a mutant from a signal transduction protein, which, when expressed, yields a hypersensitive response. These mutants preferably are encoded on the acd locus or the lsd locus. Specifically mutants would be ndr1-PKC, ndr1-cDPK and truncated Xa21.

An other embodiment of the invention is a method for the induction of pathogen resistance in plants characterized by transforming a plant with a polynucleotide sequence comprising a pathogen inducible promoter which regulates the expression of a compound which is able to alleviate the inhibitory effect of a protein on the signal transduction pathway leading to a hypersensitive response in plants. An example of such a method is a method wherein the compound is an mRNA which is coding for the inhibitory protein in an anti-sense orientation, a method wherein the compound is interacting sterically with the inhibitory protein or a method wherein the compound is an antibody, a ribozyme or an RNA molecule which is able to suppress translation of the mRNA coding for the inhibitory protein.

Also part of the invention are polynucleotides comprising a pathogen inducible promoter sequence operably linked to a protein encoding sequence which encodes a plant signal transduction protein which is active in the signal transduction pathway of a plants hypersensitive response. Preferably these transduction proteins are selected from the group comprising of ndr1, eds1 and Xa21. More generally, the signal transduction proteins are selected from the group consisting of a G-protein, a protein kinase, an AMP-cyclase and a protein phosphatase. Another example of these signal transduction proteins are mutants from a signal transduction protein, which when expressed gives rise to a hypersensitive response in plants, especially those where the mutant protein is encoded on the acd locus or the lsd locus. Specifically preferred mutants are selected from the group of ndr1-PKC, ndr1-cDPK and truncated Xa21.

Yet another embodiment of the invention are polynucleotides comprising a pathogen inducible promoter sequence operably linked to a sequence which is able to alleviate the inhibitory effect of a protein which is active in the signal transduction pathway of a plants hypersensitive response.

The pathogen-inducible promoters for these polynucleotides can be selected from the group comprising of the promoters of prp1, Fis1, Bet v 1, Vst1, gstA1, and sesquiterpene cyclase, but any pathogen-inducible promoter which is switched on after pathogen infection can be used.

Also part of the invention is a method using a polynucleotide as described above to transform a plant, making said plant at least partially resistant to pathogens.

LEGENDS TO THE FIGURES

FIG. 1. Typical transient expression assay in Onion for wt and truncated XA21 function. Panel A: bombardment with 35S-uidA alone; panel B: cobombardment of 35S-uidA and pMOG1468; panel C: cobombardment of 35S-uidA and pMOG1470; panel D: cobombardment of 35S-uidA and pMOG1475.

DETAILED DESCRIPTION

Although the invention is illustrated in detail for some transgenic plants, it should be understood that any plant species that is subject to some form of pathogen attack, especially from fungi or bacteria, may be provided with one or more plant expressible gene constructs, which when expressed are capable of inducing a HR. The invention can even be practiced in plant species that are presently not amenable for transformation, as the amenability of such species is just a matter of time and because transformation as such is of no relevance for the principles underlying the invention. Hence, plants for the purpose of this description shall include angiosperms as well as gymnosperms, monocotyledonous as well as dicotyledonous plants, be they for feed, food or industrial processing purposes; included are plants used for any agricultural or horticultural purpose including forestry and flower culture, as well as home gardening or indoor gardening, or other decorative purposes.

The invention is illustrated using signal transduction proteins which are known to play a role in the cascade of events after pathogen infection and which can induce a HR upon such an infection. In order to provide a quick and simple test if the constructs which are described here or any new constructs which are obvious to the person skilled in the art after reading this application indeed can yield a hypersensitive response the person skilled in the art can perform a rapid transient expression test known under the name of ATTA (*Agrobacterium tumefaciens* Transient expression Assay). In this assay (of which a detailed description can be found in Van den Ackerveken, G., et al., Cell 87, 1307–1316, 1996) the nucleotide sequence coding for the signal transduction protein which is to be tested is placed under control of the CaMV 35S promoter and introduced into an Agrobacterium strain which is also used in protocols for stable transformation. After incubation of the bacteria with acetosyringon or any other phenolic compound which is known to enhance Agrobacterium T-DNA transfer, 1 ml of the Agrobacterium culture is infiltrated into an in situ plant leaf (from e.g. a tobacco or tomato plant) by injection after which the plants are placed in a greenhouse. After 2–5 days the leaves can be scored for occurrence of HR symptoms.

Overexpression of Proteins.

One of the possibilities that is available to use plant proteins with a role in hypersensitive lesion formation is through direct overexpression. There are a number of ways in which a person skilled in the art can achieve over expression of a particular protein. These methods are well known and frequently used within the art. The protein that is overexpressed can be the receptor of a ligand that normally triggers the hypersensitive response or a positive acting component in the signal transduction pathway leading to a hypersensitive response. Overexpression of a positive regulator of the pathway, which can be e.g. a G-protein, AMP-cyclase, kinase or phosphatase can upset the balance present between components of the signalling pathway leading to a hypersensitive response. This in fact leads to inadvertent signalling in the absence of the ligand normally responsible for triggering of the pathway.

Downregulation, Inhibition or Inactivation of Proteins.

Another way to reach a similar effect is through downregulation, inhibition or inactivation of negative acting components within the signal transduction pathway leading to a hypersensitive response. There are a number of ways in which a person skilled in the art can achieve under expression or down regulation of a particular protein. These methods are well known and frequently used within the art.

The negative acting proteins may have a variety of functions. Well known examples are phosphatases and kinases. These represent common regulators of enzyme- and signal transduction component activity.

Pathogen-induced removal of such a protein can effectively be mediated through induced expression of antisense RNA (as outlined in Kumria et al., 1998, Current Science 74, 35–41), (short stretches of) sense RNA (sense suppression, van Blokland et al., 1994 Plant Journal 6, 861–877) or through the expression of ribozymes, sequence specific RNA-based ribonucleases (outlined in e.g. Wegener et al., 1994, Mol. Gen. Genet. 245, 465–470; Perriman et al., 1995, Proc. Natl. Acad. Sci. USA 92, 6175–6179).

More directly, expression of proteins that interfere with the normal inhibitory function of these proteins, thereby alleviating their inhibitory effect, is a possibility that is known to those skilled in the art. A specific example of such compounds are antibodies that can be expressed in plants, which may e.g. interfere sterically with the inhibitory function.

Dominant Interfering Proteins.

It is known to those skilled in the art, that mutant proteins, such as point mutants and deletion mutants derived from proteins with a role in signal transduction, can have altered properties relating to the way they are regulated. As an example, the activity of mutant proteins can be expressed in an active form continuously, whereas the activity of its non-mutated counterpart is tightly regulated (Chang & Meyerowitz, 1995, Proc. Natl. Acad. Sci. USA 92, 4129–4133; Miloso et al., 1995, J. Biol. Chem. 270, 19557–19562). When such a mutant protein can be identified/constructed from one having a positively acting role in the signal transduction pathway leading to the hypersensitive reaction, it then can be used as a tool to obtain broad-spectrum resistance. By coupling the open reading frame encoding such active mutant protein to a pathogen-inducible promoter in a functional manner, activation of the signal transduction pathway leading to the HR is directly mediated through promoter activation by pathogen infection. Likewise, dominant interfering negative acting proteins are described, (Boylan et al., 1994, Plant Cell 6, 449–460; Okamoto et al., 1997 Plant Physiol. 115, 79–85; McNellis et al., 1996, Plant Cell 8, 1491–1503; Emmler et al., 1995, Planta 197, 103–110).

Examples of mutants described to give an HR are the spontaneous HR, accelerated cell death (acd) and lesion simulating mutants (lsd) (Neuffer & Calvert, 1975, J. Hered. 66, 265–270; Dietrich et al., 1994 Cell 77, 565–577).

In both cases described above, the mutant protein used may be derived from the same plant, or from a heterologous source.

2nd Messenger Generating Systems

Yet another way to induce the signal transduction pathway leading to the hypersensitive response is through second messengers. Signal transduction leading to the hypersensitive response is known to be mediated by second messenger molecules. As an example, influx of $Ca^{2+}$-ions appears to play an important role (Cho, Abstract ISPMB congress Singapore, 1997). It is possible to generate such a stimulus by introducing a heterologous protein that allows unregulated $Ca^{2+}$ influx into the cytoplasm, setting off the downstream sequence of events that eventually lead to the hypersensitive reaction.

Method of Generating a Mutant Protein that Activates the Hypersensitive Response When a protein is identified that plays a role in the hypersensitive response, mutants can be made that are thought to be refractory to inhibitory regulation. Commonly used procedures to identify sequences of interest are known to those skilled in the art. Database searches such as Prosite, containing known modification sites are frequently used.

In the NDR1 protein, which plays a role in defense response of plants, two putative CDPK (Ca2+-dependent protein kinase) and three PKC (protein kinase C) phosphorylation sites can be identified, that could provide a good starting point searching for suitable mutants (Subramanian et al., 1997, Plant Cell 9, 653–664). Mutation of threonine and serine residues to aspartic acid and glutamic acid residues frequently leads to activation, as was shown in many proteins of which the activity is modulated by phosphorylation, e.g. in a MAPK-activated protein (Engel et al., 1995. J. Biol. Chem. 270, 27213–27291), and in a MAP-kinase-kinase protein (Huang et al., 1995 Mol. Biol. Cell 6, 237–245). Also C- and N-terminal as well as internal deletion mutants of these proteins can be tested for suitable mutants.

A more undirected way of identifying interesting mutants of which constitutive activity is induced is through propagation of the protein-encoding DNA in so-called *E. coli* 'mutator' strains.

Another protein active in the hypersensitive response is Xa21 (Wen-Yuan Song et al. 1995, science 270: 1804–1806) which is thought to be a resistance gene in rice. It has a leucine rich region and a cytoplasmatic serine-threonine kinase domain.

A rapid way of testing all made mutants for their suitability to elicit an HR is through the ATTA assay, as described above. Many mutants can be screened with low effort to identify those that will elicit an HR upon expression.

Proteins of the invention, also denominated as signal transduction proteins, include all proteins known or to be detected which play a role in the signal transduction pathway(s) of plants which lead to a hypersensitive response. These include proteins that are components of this pathway up from the first proteins that transfer the signal which is generated by the elicitor protein interacting with the receptor moiety down to the proteins which actually cause the HR, regulatory proteins in this pathway, proteins which can affect the inhibitory effects of pathway inhibitors and 2nd messenger generating enzymes. It should be understood that anti-sense suppression or co-suppression of inhibitory components should also be caught under this definition.

The word protein means a sequence of amino acids connected trough peptide bonds. Polypeptides or peptides are also considered to be proteins. Homologues of the signal transduction proteins which are part of the invention are proteins that are encoded by DNA sequences found to hybridize under stringent conditions with nucleotide sequences coding for said signal production proteins. Such homologues can be found in heterologous species but they can also be made by protein engineering in vivo, e.g. by changing the open reading frame capable of encoding the signal transduction proteins. Mutations are made by replacing, adding and/or deleting one or more amino acids, while still retaining their HR inducing activity. As long as the changes in the amino acid sequences do not altogether abolish the HR inducing activity such homologues are embraced in the present invention. In addition to this, conservative amino acid replacements may be made within these mutated proteins which do not affect activity. In particular conservative amino acid replacements may be made between the following groups, Viz.

(a) Alaninie, Serine, Glycine and Threonine (b) Glutamic acid and Aspartic acid (c) Arginine and Lysine (d) Isoleucine, Leucine, Valine and Methionine (e) Phenylalanine, Tyrosine and Tryptophan Further, it should be understood that mutations should be derivable from the proteins or the DNA sequences encoding these proteins depicted in the sequence listing while retaining biological activity, i.e. all, or a great part of the intermediates between the mutated protein and the protein depicted in the sequence listing should have HR-response inducing activity. A great part would mean 30% or more of the intermediates, preferably 40% of more, more preferably 50% or more, more preferably 60% or more, more preferably 70% or more, more preferably 80% or more, more preferably 90% or more, more preferably 95% or more, more preferably 99% or more.

The present invention provides a chimeric DNA sequence which comprises a pathogen inducible promoter which regulates the expression of a plant protein or a homologue thereof which is capable of eliciting a hypersensitive response. The expression chimeric DNA sequence shall mean to comprise any DNA sequence which comprises DNA sequences not naturally found in nature. The said open reading frame may be incorporated in the plant genome wherein it is not naturally found, or in a replicon or vector where it is not naturally found, such as a bacterial plasmid or a viral vector. Chimeric DNA shall not be limited to DNA molecules which are replicable in a host, but shall also mean to comprise DNA capable of being ligated into a replicon, for instance by virtue of specific adaptor sequences, physically linked to the nucleotide sequence according to the invention.

The open reading frame coding for the signal transduction protein may be derived from a genomic library. In this latter it may contain one or more introns separating the exons making up the open reading frame that encodes the protein. The open reading frame may also be encoded by one uninterrupted exon, or by a cDNA to the mRNA encoding the signal transduction protein. Open reading frames according to the invention also comprise those in which one or more introns have been artificially removed or added. Each of these variants is embraced by the present invention.

Pathogen inducible promoters are known in the art and are responsive to a large number of pathogens and to a specific elicitors produced by these pathogens. Examples of such pathogen inducible promoters are: the prp1 promoter (Martini, N., et al., Mol. Gen. Genet. 236, 179–186, 1993), the Fis1 promoter (WO 96/34949), the Bet v 1 promoter (Swoboda, I., et al., Plant, Cell and Env. 18, 865–874, 1995), the Vst1 promoter (Fischer, R., Dissertation, Univ. of Hohenheim, 1994; Schubert, R., et al. Plant Mol. Biol. 34, 417–426, 1997), the sesquiterpene cyclase promoter (Yin, S., et al., Plant Physiol. 115, 437–451, 1997) and the gstA1 promoter (Mauch, F. and Dudler, R., Plant Physiol. 102, 1193–1201, 1993). Several other promoters are known in the art and can be used for the nucleotide sequences of this invention.

In eukaryotic cells, an expression cassette usually further comprises a transcriptional termination region located downstream of the open reading frame, allowing transcription to terminate and polyadenylation of the primary transcript to occur. In addition, the codon usage may be adapted to accepted codon usage of the host of choice. The principles governing the expression of a chimeric DNA construct in a chosen host cell are commonly understood by those of ordinary skill in the art and the construction of expressible chimeric DNA constructs is now routine for any sort of host cell, be it prokaryotic or eukaryotic.

In order for the open reading frame to be maintained in a host cell it will usually be provided in the form of a replicon comprising said open reading frame according to the invention linked to DNA which is recognised and replicated by the chosen host cell. Accordingly, the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. A particularly preferred form of Ti-plasmid vectors are the so-called binary vectors as claimed in (EP 0 120 516 B1 and U.S. Pat. No. 4,940,838). Other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimeric DNA sequence according to the invention in their genome" shall mean to comprise cells, as well as multicellular organisms comprising such cells, or essentially consisting of such cells, which stably incorporate said chimeric DNA into their genome thereby maintaining the chimeric DNA, and preferably transmitting a copy of such chimeric DNA to progeny cells, be it through mitosis or meiosis. According to a preferred embodiment of the invention plants are provided, which essentially consist of cells which incorporate one or more copies of said chimeric DNA into their genome, and which are capable of transmitting a copy or copies to their progeny, preferably in a Mendelian fashion. By virtue of the transcription and translation of the chimeric DNA according to the invention in some or all of the plant's cells, those cells that produce the antifungal protein will show enhanced resistance to fungal infections.

Transformation of plant species is now routine for an impressive number of plant species, including both the Dicotyledoneae as well as the Monocotyledoneae. In principle any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (Crossway A. et al., 1986, Mol. Gen. Genet. 202, 179–185), (DNA or RNA-coated) particle bombardment of various plant material (Klein T. M. et al., 1987, Nature 327, 70), infection with (non-integrative) viruses and the like. A preferred method according to the invention comprises Agrobacterium-mediated DNA transfer. Especially preferred is the use of the so-called binary vector technology as disclosed in EP A 120 516 and U.S. Pat. No. 4,940,838.

Generally, after transformation plant cells or cell groupings are selected for the presence of one or more markers which are encoded by plant expressible genes co-transferred with the nucleic acid sequence according to the invention, whereafter the transformed material is regenerated into a whole plant.

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto, et al, 1989, Nature 338, 274–276). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–61 8). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as rice and corn are also amenable to DNA transfer by Agrobacterium strains (vide WO 94/00977; EP 0 159 418 B1; Gould J, Michael D, Hasegawa O, Ulian E C, Peterson G, Smith R H, (1991) Plant. Physiol. 95, 426–434).

Following DNA transfer and regeneration, putatively transformed plants may be evaluated, for instance using Southern analysis, for the presence of the chimeric DNA according to the invention, copy number and/or genomic organization. After the initial analysis, which is optional, transformed plants showing the desired copy number and expression level of the newly introduced chimeric DNA according to the invention may be tested for resistance levels against a pathogen.

Other evaluations may include the testing of pathogen resistance under field conditions, checking fertility, yield, and other characteristics. Such testing is now routinely performed by persons having ordinary skill in the art.

Following such evaluations, the transformed plants may be grown directly, but usually they may be used as parental lines in the breeding of new varieties or in the creation of hybrids and the like.

These plants, including plant varieties, with improved resistance against pathogens may be grown in the field, in the greenhouse, or at home or elsewhere. Plants or edible parts thereof may be used for animal feed or human consumption, or may be processed for food, feed or other purposes in any form of agriculture or industry. Agriculture shall mean to include horticulture, arboriculture, flower culture, and the like. Industries which may benefit from plant material according to the invention include but are not limited to the pharmaceutical industry, the paper and pulp manufacturing industry, sugar manufacturing industry, feed and food industry, enzyme manufacturers and the like.

The advantages of the plants, or parts thereof, according to the invention are the decreased need for pesticide treatment, thus lowering costs of material, labour, and environmental pollution, or prolonging shelf-life of products (e.g. fruit, seed, and the like) of such plants. Plants for the purpose of this invention shall mean multicellular organisms capable of photosynthesis, and subject to some form of pathogen induced disease. They shall at least include angiosperms as well as gymnosperms, monocotyledonous as well as dicotyledonous plants.

The invention will now be described by way of the following non-limiting examples. It will be apparent to the skilled artisan that the following techniques can be varied and modified without detracting from the gist of the present invention.

EXPERIMENTAL PART

Standard methods for the isolation, manipulation and amplification of DNA, as well as suitable vectors for replication of recombinant DNA, suitable bacterium strains, selection markers, media and the like are described for instance in Maniatis et al., molecular cloning: A Laboratory Manual 2nd. edition (1989) Cold Spring Harbor Laboratory Press; DNA Cloning: Volumes I and II (D. N. Glover ed. 1985); and in: From Genes To Clones (E.-L. Winnacker ed. 1987).

Example 1

Isolation and Cloning of the ndr1 Gene

The sequence of the ndr1 gene (non-race specific disease resistance) from *Arabidopsis thaliana* was published (Genbank accession number AF021346 Century K. S., Science, Vol.278, 12 Dec. 1997 pp.1964–1965). Based on this sequence (SEQ ID NO:13) the primers FR-Ndr-297 (SEQ ID NO:1) 5'-CAA GAA TTC GGT CAT GAA TAA TCA AAA TGA AGA CAC-3', introducing a EcoRI site and, downstream, a RcaI site at the start codon and FR-Ndr-298 (SEQ ID NO:2) 5'-ATT AGG ATC CTT AAC GAA TAG CAA AGA ATA CGA G-3', introducing a BamHI site behind the stopcodon were synthesised to amplify Nrd1 with Pfu turbo DNA polymerase (Stratagene) from genomic DNA of *Arabidopsis thaliana* colombia (PCR program 1' 95° C., 1' 43° C., 2' 72° C., 4 cycles; 1' 95° C., 1' 55° C., 2' 72° C., 25 cycli). The PCR product was digested with EcoRI and BamHI yielding a 660 bp fragment that was cloned in pBKS (Stratagene) that was digested with the same restriction enzymes. The sequence of the PCR product was confirmed by DNA sequencing. The ndr1 ORF was subsequently ligated between the 35S promoter joined with the GluII 5' untranslated region (Linthorst et al., 1990, Proc. Natl. Acad. Sci. USA 87: 8756–8760) (SEQ ID NO:17) and the 3' untranslated region of the potato proteinase inhibitor II gene (Thornburg et al., 1987, Proc. Natl. Acad. Sci. USA 84, 744–748) which contains sequences needed for polyadenylation (An et al., 1989, Plant cell 1, 115–122). The complete expression unit was then transferred as a SacI-EcoRI fragment to the binary vector pMOG800 (described inter alia in WO 98/13478) resulting in pMOG1456. This construct was electroporated in EHA105 for ATTA experiments.

Example 2

Constructing of Modified ndr1

To make a constitutive active Nrd1 protein potential PKC (protein kinase C) or CDPK (Ca2+dependent protein kinase) sites were modified by replacing the codon Serine or Threonine for an Aspartate codon.

Potential PKC sites were changed in the ndr1 gene at amino acid Ser-35, Thr-94 and Thr-164 (SEQ ID NO:14) using the following primers:

FR-Ndr-297 (SEQ ID NO:1): 5'-CAAGAATTCGGTCA TGAATAATCAAAATGAAGACAC-3' FR-Ndr-298 (SEQ ID NO:2): 5'-ATTAGGATCCTTAACGAATAG CAAAGAATACGAG-3'

(for amplification of the ndr1 ORF)

FR-Ndr-303 (SEQ ID NO:7): 5'-CTTATGGCTTG ATCTCCGTGCGGAC-3' FR-Ndr-304 (SEQ ID NO:8): 5'-CGCACGGAGATCAAGCCATAAGAAA AGA-3'

(ser-35=>asp-35)

FR-Ndr-305 (SEQ ID NO:9): 5'-CCACCATCAAC GATACCAAGATCAATTCC-3' FR-Ndr-306 (SEQ ID NO:10): 5'-GATCTTGGTATCGTTGATGGTGGAA AAATTAAGG-3'

(thr-94=>asp-94)

FR-Ndr-307 (SEQ ID NO:11): 5'-GGAAAGATAA GAGGTATGGGGTTG-3' FR-Ndr-308 (SEQ ID NO: 12): 5'-CCATACCTCTTATCTTTCCAAAAAAC-3'

(thr-1 64=>asp-164)

Using these primers and pMOG1456 as a template ndr1 was mutated on all three PKC sites in one construct using Pfu turbo DNA polymerase (PCR 1' 95° C., 1' 43° C., 1.5' 72° C., 4 cycli, 1' 95° C., 1' 51° C., 1.5' 72° C., 25 cycli). In a first PCR step the following primer combinations were used to generate the mutations: 1) FR-Ndr-297 (SEQ ID NO:1)+FR-Ndr-304 (SEQ ID NO:8); 2) FR-Ndr-303 (SEQ ID NO:7)+FR-Ndr-306 (SEQ ID NO:10; 3) FR-Ndr-305 (SEQ ID NO:9)+FR-Ndr-308 (SEQ ID NO:12); 4) FR-Ndr-307 (SEQ ID NO:11)+FR-Ndr-298 (SEQ ID NO:2). In the next PCR steps the fragments were joined with the SOE technique (Splicing by Overlap Extension; Methods in Molecular Biology, Vol67: PCR Cloning Protocols; From Molecular Cloning to Genetic Engineering) and after digestion with BamHI and EcoRI the resulting PCR fragment was cloned in pBKS. After sequencing this clone, ndr1-PKC (SEQ ID NO:15) contained one point mutation at position 297 in which an A was substituted for a C. This mistake was introduced by primer FR-Ndr-305 but did not result in an amino acid change. Therefore it was decided to continue with this construct. The ndr1-PKC ORF was subsequently ligated between the 35S promoter/GluII-leader (SEQ ID NO:17) and the 3' untranslated region of the potato proteinase inhibitor II gene (Thornburg et al., 1987, Proc. Natl. Acad. Sci. USA 84, 744–748) which contains sequences needed for polyadenylation (An et al., 1989, Plant cell 1, 115–122).

The complete expression unit was then transferred as a SacI-EcoRI fragment to binary vector pMOG800 resulting in pMOG1457. This construct was electroporated in EHA105 for ATTA experiments.

Potential CDPK sites were changed at ser-20 and ser-207 (SEQ ID NO.14) using the following primers:

FR-Ndr-297 (SEQ ID NO.1): 5'-CAAGAATTCGGTC ATGAATAATCAAAATGAAGACAC-3' FR-Ndr-298 (SEQ ID NO.2): 5'-ATTAGGATCCTTAACGAATAG CAAAGAATACGAG-3'
(for amplification of the ndr1 ORF)
FR-Ndr-299 (SEQ ID NO.3): 5'-TGCTTAGATTTC ATCTTCACAGC-3' FR-Ndr-300 (SEQ ID NO.4): 5'-TGTGAAGATGAAATCTAAGCAGCAAG-3' (ser-20=>asp-20)
FR-Ndr-301 (SEQ ID NO.5): 5'-CCGATTGATGTT TTGATGAATTTAC-3' FR-Ndr-302 (SEQ ID NO.6): 5'-TTCATCAAAACATCAATCGGAAAAGAG-3' (ser-207=>asp-207)

With these primers and pMOG1456 as a template ndr1 was mutated on the two CDPK sites using PCR as described for ndr1-PKC. The resulting fragment was digested with BamHI and EcoRI and cloned in pBKS. The correct sequence of the PCR product was confirmed with DNA sequencing (SEQ ID NO.16). The Nrd1-CDPK ORF was subsequently ligated between the 35S promoter/35s-GluII leader (SEQ ID NO:17) and 3' untranslated region of the potato proteinase inhibitor II gene (Thornburg et al., 1987, Proc. Natl. Acad. Sci. USA 84, 744–748) which contains sequences needed for polyadenylation (An et al., 1989, Plant cell 1, 115–122). The complete expression unit was then transferred as a SacI-EcoRI fragment to the binary vector pMOG800.

This construct was electroporated in EHA105 for ATTA experiments.

Example 3

ATTA Experiments

ATTA (*Agrobacterium tumefaciens* Transient expression assay) was carried out essentially as described by Van den Ackerveken G., et al., Cell 87, 1307–1316, 1996, with the exception that plants were incubated in the phytochamber after infiltration without a transparant bag.

Experiments were done with pMOG1456 (ndr1), pMOG1457 (ndr1-PKC), pMOG1458 (ndr1-cDPK) and pMOG1047 (35S-GUS) as a negative control. These constructs were all available in EHA105.

The results of the ATTA experiment using the ndr1 clone and the two mutants, ndr1-PKC and ndr1-CDPK, are presented in Table 1.

Table 1: ATTA in leaves of several crops to score for HR development caused by expression of ndr1 and mutants thereoff.

|  | pMOG1456 ndr1-WT | pMOG1457 ndr1-PKC | pMOG1458 ndr1-cDPk | pMOG1047 GUS |
|---|---|---|---|---|
| SR1 | + | + | + | – |
| Tomato | – | + | + | – |
| *Brassica napus* | – | + | + | – |

Example 4

Construction of ndr1 and Derivatives Under Control of a Pathogen Inducible Promoter The openreading frame of the ndr1 gene and the modified ndr1 genes were ligated between the prp1 promoter (Martini et al., MOL. Gen. Genet. (1993) 236:179–185) and the 3' untranslated region of the potato proteinase inhibitor II gene (Thornburg et al., 1987, Proc. Natl. Acad. Sci. USA 84, 744–748) which contains sequences needed for polyadenylation (An et al., 1989, Plant cell 1, 115–122)in the high copy vector pBS (Stratagene). The complete expression unit was then transferred as a BamHI-EcoRI fragment to the binary vector pMOG800 resulting in pMOG1459 (ndr1), pMOG1460 (ndr1-PKC) and pMOG1461 (ndr1-cDPK). The Agrobacterium strain MOG101 was produced according to the method described in WO96/21030.

The constructs pMOG1459, pMOG1460 and pMOG1461 were then electroporated into MOG101 in preparation for transformation of tobacco.

Example 5

Transformation of Tobacco with the Constructs pMOG1459, pMOG1460 and pMOG1461

Tobacco was transformed by co-cultivation of plant tissue with *Agrobacterium tumefaciens* strain MOG101 containing the vector of interest as described above. Transformation was carried out using co-cultivation of tobacco leaf disks as described by Horsch et al. (1985) Science 227, 1229. Transgenic plants were regenerated from shoots that grow on selection medium containing kanamycin, rooted and then transferred to soil.

Example 6

Infection Assay of ndr1, ndr1-PKC and ndr1-CDPK Tobacco Transgenics with *Oidium lycopersicon*

Tobacco plants with prp1-ndr1 (pMOG1459), prp1-ndr1-PKC (pMOG1460), prp1-ndr1-CDPK (pMOG1461) and 2 control constructs, prp1-½-GUS (pMOG1058) and Ferredoxin-ro1D-GUS (pMOG1059) were tested for resistance to *Oidium lycopersicon*.

In vitro grown plants were transplanted to potting soil and moved to a growthroom for 14 days. After these two weeks, the plants were placed in a testroom with 16 h light/8 h dark, 20° C. and 80% RH and were inoculated with the pathogen when they had been in the testroom for 3 days (17 days after potting).

Inoculation was done by spraying at least 10 plants per construct with a spore suspension of *O. Lvcopersicon* containing $3 \times 10^4$ spores/ml (total volume used: 1 liter).

Disease severity (% leaf area covered by powdery mildew) was measured as soon as the first infection symptoms were visible. The infection started 9 days after inoculation and was equally distributed over all the plants but too low to give a clear disease severity. The first disease severity data were collected 14 days after inoculation.

From the results it can be learned that one plant transformed with pMOG1461 showed to be resistant to fungal infection.

Example 7

Isolation of the Xa21 Gene from *O.sativa* ssp. Indica Line, IRBB21

The predicted amino acid sequence (SEQ ID NO: 18) and the deduced protein domains of Xa21 have been published (Wen-Yuan Song et al., 1995, Science 270: 1804–1806). The GenBank accession number for Xa21 genomic and cDNA sequences is U37133.

For the isolation of the Xa21 gene mRNA was isolated from leafmaterial of O.sativa ssp. Indica line, IRBB21 using the QuickPrep® Micro mRNA Purification Kit of Pharmacia. First strand cDNA was synthesised using SuperScript™ Rnase H-Reverse Transcriptase from GibcoBRL following the instructions of the manufacture. Primers FR-Xa21-362 (SEQ ID NO: 19) 5' CCG GTA CCT CAT GAT ATC ACT CCC ATT ATT GC 3' and FR-Xa21-363 (SEQ ID NO: 20) 5' GGA GAT CTT CAG AAT TCA AGG CTC CCA CC 3' were used to PCR the complete CDS of Xa21. Primer FR-Xa21-362 introduces a RcaI site on the ATG of Xa21 and a KpnI site at the 5' end of the PCR-product. Primer FR-Xa21-363 introduces a BglII site directly behind the stopcodon of Xa21. Using PfuTurbo™ DNA Polymerase (Stratagene) and the primers FR-Xa21-362 and FR-Xa21-363 the Xa21 gene was amplified from first strand cDNA. Amplification was started by melting for 2' at 95° C., followed by 30 cycli for 1' at 95° C., 1' at 55° C. and 6' at 72° C. and ended with an extension period at 72° C. for 10'. The PCR yielded a 3.1 kb fragment that was digested with BglII and KpnI and ligated in pUC28 digested with the same enzymes. The vector pUC28 (SEQ ID NO: 27) was constructed from pUC18 (J. Messing, 1983, New M13 vectors for cloning, Methods Enzymology, vol. 101:20) by ligation of adapter

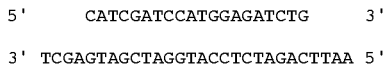

in the EcoRI and SstI site of pUC18. A ClaI, NcoI and BglII site are thus added to the multiple cloning site of pUC18.

The correct sequence of the PCR-product was confirmed by sequence analysis.

The complete CDS of Xa21 was cut out from the pUC28 vector by digestion with RcaI and BglII. This fragment was cloned between the 35S promoter/gluII leader (SEQ ID NO:17) and the 3' untranslated region of the potato proteinase inhibitor II gene. The resulting plasmid was named pMOG1468.

Example 8

Cloning of Truncated Versions of Xa21

Two truncated versions of the Xa21 gene were both cloned between the 35S promoter/gluII leader (SEQ ID NO:17) and the 3' untranslated region of the potato proteinase inhibitor II gene.

For cloning of truncation 1 two primers were developed: FR-Xa21-369 (SEQ ID NO: 21) 5' CCT TCA AGA ACT TTC ATG AAA GGC CAC CC 3' and FR-Xa21-370 (SEQ ID NO: 22) 5' CTC CCG GAT CCT CAC ACT GGA AAC AAT CC 3'. Truncation 1 uses M690 of Xa21 as a start codon and V1017 of Xa21 (see SEQ ID NO:18 for amino acid references) as last codon. Primer FR-Xa21-369 introduces an RcaI site at the ATG of M690 and primer FR-Xa21-370 introduces a stopcodon and a BamHI site directly behind V1017. Using PfuTurbo™ DNA Polymerase (Stratagene) and the primers FR-Xa21-369 and FR-Xa21-370 truncation 1 was amplified from pMOG1468. Amplification was started by melting for 1' at 95° C., followed by 25 cycli for 1' at 95° C., 1' at 60° C. and 1'30" at 72° C. and ended with an extension period at 72° C. for 10'. PCR yielded the expected 1015 bp fragment. This fragment was cloned between the 35S promoter/gluII leader (SEQ ID NO:17) and the 3' untranslated region of the potato proteinase inhibitor II gene. The resulting plasmid was named pMOG1470.

For cloning of truncation 2 three primers were developed: FR-PR1a-371 (SEQ ID NO: 23) 5' CAA TTA TCA TGA GAT TTG TTC TCT TTT C 3', FR-Xa21-372 (SEQ ID NO: 24) 5' GGC AGA TGT AGA TCG GCA CGG CAA GAG TG 3' and FR-Xa21-373 (SEQ ID NO: 25) 5° CAC TCT TGC CGT GCC GAT CTA CAT CTG CC 3'. In this truncation part of the Xa21 CDS (D635-V1017) is fused to the C-terminus of the PR-1a signal peptide (SEQ ID NO:26) (Cornelissen et al., 1987, Nucleic Acid Research 15: 6799–6811). The fusion is established by overlap extension as described.

Primer FR-PR1a-371 introduces a RcaI site on the ATG of M1 of the PR-1a signal sequence. As a consequence the second amino acid changes from G to R. Primer FR-Xa21-372 has homology with the last 5 amino acids of the signal peptide PR-1a and with the first 4⅔ amino acids of Xa21. Using PfuTurbo™ DNA Polymerase (Stratagene) and the primers FR-PR1a-371 and FR-Xa21-372 the tobacco PR-1a signal peptide was amplified from tobacco genomic DNA. Amplification was started by melting for 1' at 95° C., followed by 35 cycli for 1' at 95° C., 1' at 50° C. and 20" at 72° C. and ended with an extension period at 72° C. for 10'. The expected 114 bp PCR-product was cut from a 2% agarose gel and DNA was extracted with QIAGEN Gelextraction Kit.

Primer FR-Xa21-370 introduces a stopcodon and a BamHI site directly behind V1017 of Xa21 and primer FR-Xa21-373 is homologous to the sequence encoding the last 5 amino acids of the signal peptide PR-1a and to the first 4⅔ amino acids of Xa21. Using PfuTurbo™ DNA Polymerase (Stratagene) and the primers FR-PR1a-370 and FR-Xa21-373 the Xa21 part was amplified from pMOG1468. Amplification was started by melting for 1' at 95° C., followed by 25 cycli for 1' at 95° C., 1' at 40° C. and 1'30" at 72° C. and ended with an extension period at 72° C. for 10'. The expected 1.2 kb PCR-product was purified with QIAGEN PCR Purification Kit.

The fusion between the signal peptide PR-1a and the Xa21 was accomplished by overlap extension with primers FR-PR1a-371 and FR-Xa21-370. Amplification, with PfuTurbo™ DNA Polymerase, was started by melting for 1' at 95° C., 3 cycli for 1' at 95° C., 1' at 50° C. and 1'30" at 72° C. followed by 22 cycli for 1' at 95° C., 1' at 55° C. and 1'30" at 72° C. and ended with an extension period at 72° C. for 10'. The expected 1265 bp PCR-product was purified with QIAGEN PCR Purification Kit and digested with BamHI and RcaI. This fragment was then cloned between the 35S promoter/gluII leader (SEQ ID NO:17) and the 3' untranslated region of the potato proteinase inhibitor II gene. The resulting plasmid was named pMOG1475.

Example 9

Transient Expression Assay for Xa21, and Derivatives, Function

A biolistic system was chosen for gene delivery in monocot tissue (Onion) to study whether Xa21 and truncated versions of Xa21 (Example 8) can elicit a HR in monocot tissue. The assay was carried out essentially as described by Mindrinos et al. (1994, Cell 78: 1089–1099). FIG. 1 showes a typical result of such a biolistic experiment. Compared to the GUS control construct (35S-uidA), co-bombardment of the 35S-uidA construct with either pMOG1468, pMOG1470 or pMOG1475 resulted in a reduced density of blue spots after GUS staining. Construct pMOG1475 showes the strongest reduction in blue spots, which was in all experiments (at least 3 repeats) less than 10% of the 35S-uidA control.

What is claimed is:

1. A method for the induction of pathogen resistance in a plants, comprising:
   (a) providing a polynucleotide sequence encoding a constitutively active mutated ndr1 protein, wherein the mutation consists of an amino acid substitution at a position relative to SEQ ID NO. 14 selected from the group consisting of Ser-20, Ser-35, Thr-94, Thr-164 and Ser-207;
   (b) producing a chimeric DNA sequence by operably linking said polynucleotide sequence to a pathogen-inducible promoter;
   (c) transforming a plant cell with said chimeric DNA sequence;
   (d) regenerating from said plant cell a plant wherein infection of said plant by a pathogen causes activation of said pathogen-inducible promoter, said activation resulting in expression of said constitutively active mutated ndr1 and wherein said expression gives rise to a hypersensitive response.

2. The method according to claim 1, wherein said mutated ndr1 protein is encoded by the polynucleotide sequence set forth in SEQ ID NO: 15 or SEQ ID NO: 16.

3. The method according to claim 1, wherein the transformed plant is resistant to pathogens.

4. A chimeric polynucleotide comprising a pathogen inducible promoter sequence operably linked to a polynucleotide sequence encoding a constitutively active mutated ndr1 protein which is active in the plant-signal transduction pathway of a plant's hypersensitive response, wherein the mutation consists of an amino acid substitution at a position relative to SEQ ID NO. 14 selected from the group consisting of Ser-20, Ser-35, Thr-94, Thr-164 and Ser-207.

5. The chimeric polynucleotide according to claim 4, wherein the mutated ndr1 protein is encoded by the polynucleotide sequence set forth in SEQ ID NO: 15 or SEQ ID NO: 16.

6. The chimeric polynucleotide according to claim 4, wherein the pathogen inducible promoter is selected from the group consisting of the promoters of prp1, Fis1, Bet v 1, Vst1, gstA1, and sesquiterpene cyclase.

* * * * *

SEQUENCE LISTING

<160> NUMBER OF SEQ ID NOS: 29

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 1
caagaattcg gtcatgaata atcaaaatga agacac                              36

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 2
attaggatcc ttaacgaata gcaaagaata cgag                                34

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 3
tgcttagatt tcatcttcac agc                                            23

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 4
tgtgagatga aatctaagca gcaag                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 5
ccgattgatg ttttgatgaa tttac                                          25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 6
ttcatcaaaa catcaatcgg aaaagag                                        27

<210> SEQ ID NO 7
<211> LENGTH: 25

```
<212> TYPE: DNA
<213> ORGANISM: Artificial Sequence
<220> FEATURE:
<223> OTHER INFORMATION: Description of Artificial Sequence:Primer

<400> SEQUENCE: 7
cttatggctt gatctccgtg cggac                                      25

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 8
cgcacggaga tcaagccata agaaaaga                                   28

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 9
ccaccatcaa cgataccaag atcaattcc                                  29

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 10
gatcttggta tcgttgatgg tggaaaaatt aagg                            34

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 11
ggaaagataa gaggtatggg gttg                                       24

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 12
ccatacctct tatctttcca aaaaac                                     26

<210> SEQ ID NO 13
<211> LENGTH: 668
<212> TYPE: DNA
<213> ORGANISM: Arabidopsis thaliana

<400> SEQUENCE: 13
tcatgaataa tcaaaatgaa gacacagaag gtggtcgaaa ctgttgtact tgctgcttaa    60
```

-continued

```
gcttcatctt cacagctggt ctcacctctc ttttcttatg gcttagtctc cgtgcggaca      120
aacccaaatg ctcaatccaa aacttttca ttcctgccct cggaaaagac ccaaattcac      180
gagacaatac cactctaaat ttcatggttc gttgtgacaa tccgaataaa gacaaaggaa      240
tctactacga cgatgtccac cttaatttt ccaccatcaa cacgaccaag atcaattcat      300
ctgctcttgt cttagttggt aactacacag tgcctaagtt ctatcaagga cacaagaaga      360
aggccaagaa gtggggtcaa gtaaagccgc taaacaacca gacggtttta cgagcggttt      420
tgcctaatgg atcggctgtt ttcaggttgg atctcaagac tcaagttaga ttcaagattg      480
ttttttggaa aactaagagg tatggggttg aagttggagc tgatgttgaa gtcaacggtg      540
atggagttaa agctcagaag aaaggaatta agatgaagaa atctgattct tcttttccat      600
taagaagctc ttttccgatt agtgttttga tgaatttact cgtattcttt gctattcgtt      660
aaggatcc                                                              668
```

<210> SEQ ID NO 14
<211> LENGTH: 220
<212> TYPE: PRT
<213> ORGANISM: Arabidopsis thaliana

<400> SEQUENCE: 14

```
Met Asn Gln Asn Glu Asp Thr Glu Gly Gly Arg Asn Cys Cys Thr
 1               5                  10                  15

Cys Cys Leu Ser Phe Ile Phe Thr Ala Gly Leu Thr Ser Leu Phe Leu
                20                  25                  30

Trp Leu Ser Leu Arg Ala Asp Lys Pro Lys Cys Ser Ile Gln Asn Phe
            35                  40                  45

Phe Ile Pro Ala Leu Gly Lys Asp Pro Asn Ser Arg Asp Asn Thr Thr
        50                  55                  60

Leu Asn Phe Met Val Arg Cys Asp Asn Pro Asn Lys Asp Lys Gly Ile
65                  70                  75                  80

Tyr Tyr Asp Asp Val His Leu Asn Phe Ser Thr Ile Asn Thr Thr Lys
                85                  90                  95

Ile Asn Ser Ser Ala Leu Val Leu Val Gly Asn Tyr Thr Val Pro Lys
            100                 105                 110

Phe Tyr Gln Gly His Lys Lys Ala Lys Lys Trp Gly Gln Val Lys
        115                 120                 125

Pro Leu Asn Asn Gln Thr Val Leu Arg Ala Val Leu Pro Asn Gly Ser
    130                 135                 140

Ala Val Phe Arg Leu Asp Leu Lys Thr Gln Val Arg Phe Lys Ile Val
145                 150                 155                 160

Phe Trp Lys Thr Lys Arg Tyr Gly Val Glu Val Gly Ala Asp Val Glu
                165                 170                 175

Val Asn Gly Asp Gly Val Lys Ala Gln Lys Lys Gly Ile Lys Met Lys
            180                 185                 190

Lys Ser Asp Ser Ser Phe Pro Leu Arg Ser Ser Phe Pro Ile Ser Val
        195                 200                 205

Leu Met Asn Leu Leu Val Phe Phe Ala Ile Arg Glx
    210                 215                 220
```

<210> SEQ ID NO 15
<211> LENGTH: 668
<212> TYPE: DNA
<213> ORGANISM: Artificial Sequence
<220> FEATURE:
<223> OTHER INFORMATION: Description of Artificial Sequence:ndr1-PKC

<400> SEQUENCE: 15

```
tcatgaataa tcaaaatgaa gacacagaag gtggtcgaaa ctgttgtact tgctgcttaa      60
gcttcatctt cacagctggt ctcacctctc ttttcttatg gcttgatctc cgtgcggaca     120
aacccaaatg ctcaatccaa aacttttca ttcctgccct cggaaaagac ccaaattcac     180
gagacaatac cactctaaat ttcatggttc gttgtgacaa tccgaataaa gacaaaggaa     240
tctactacga cgatgtccac cttaattttt ccaccatcaa cgataccaag atcaattcct     300
ctgctcttgt cttagttggt aactacacag tgcctaagtt ctatcaagga cacaagaaga     360
aggccaagaa gtggggtcaa gtaaagccgc taaacaacca gacggtttta cgagcggttt     420
tgcctaatgg atcggctgtt ttcaggttgg atctcaagac tcaagttaga ttcaagattg     480
tttttttgga agataagagg tatggggttg aagttggagc tgatgttgaa gtcaacggtg     540
atggagttaa agctcagaag aaaggaatta agatgaagaa atctgattct tcttttccat     600
taagaagctc ttttccgatt agtgttttga tgaatttact cgtattcttt gctattcgtt     660
aaggatcc                                                              668
```

<210> SEQ ID NO 16
<211> LENGTH: 668
<212> TYPE: DNA
<213> ORGANISM: Artificial Sequence
<220> FEATURE:
<223> OTHER INFORMATION: Description of Artificial Sequence:ndr1-CDPK

<400> SEQUENCE: 16

```
tcatgaataa tcaaaatgaa gacacagaag gtggtcgaaa ctgttgtact tgctgcttag      60
atttcatctt cacagctggt ctcacctctc ttttcttatg gcttagtctc cgtgcggaca     120
aacccaaatg ctcaatccaa aacttttca ttcctgccct cggaaaagac ccaaattcac     180
gagacaatac cactctaaat ttcatggttc gttgtgacaa tccgaataaa gacaaaggaa     240
tctactacga cgatgtccac cttaattttt ccaccatcaa cacgaccaag atcaattcat     300
ctgctcttgt cttagttggt aactacacag tgcctaagtt ctatcaagga cacaagaaga     360
aggccaagaa gtggggtcaa gtaaagccgc taaacaacca gacggtttta cgagcggttt     420
tgcctaatgg atcggctgtt ttcaggttgg atctcaagac tcaagttaga ttcaagattg     480
tttttttgga aactaagagg tatggggttg aagttggagc tgatgttgaa gtcaacggtg     540
atggagttaa agctcagaag aaaggaatta agatgaagaa atctgattct tcttttccat     600
taagaagctc ttttccgatt gatgttttga tgaatttact cgtattcttt gctattcgtt     660
aaggatcc                                                              668
```

<210> SEQ ID NO 17
<211> LENGTH: 907
<212> TYPE: DNA
<213> ORGANISM: Artificial Sequence
<220> FEATURE:
<223> OTHER INFORMATION: Description of Artificial Sequence:Combination
      of 35S Promoter with the Glucanase II leader

<400> SEQUENCE: 17

```
ggatccccccg taccaattct actccaaaaa tatcaaagat acagtctcag aagaccaaag      60
ggcaattgag acttttcaac aaagggtaat atccggaaac ctcctcggat tccattgccc     120
agctatctgt cactttattg tgaagatagt ggaaaaggaa ggtggctcct acaaatgcca     180
tcattgcgat aaaggaaagg ccatcgttga agatgcctct gccgacagtg gtcccaaaga     240
```

-continued

```
tggacccca cccacgagga gcatcgtgga aaaagaagac gttccaacca cgtcttcaaa    300
gcaagtggat tgatgtgata attccgcatg gagtcaaaga ttcaaataga ggacctaaca    360
gaactcgccg taaagactgg cgaacagttc atacagagtc tcttacgact caatgacaag    420
aagaaaatct tcgtcaacat ggtggagcac gacacacttg tctactccaa aaatatcaaa    480
gatacagtct cagaagacca aagggcaatt gagacttttc aacaaagggt aatatccgga    540
aacctcctcg gattccattg cccagctatc tgtcacttta ttgtgaagat agtggaaaag    600
gaaggtggct cctacaaatg ccatcattgc gataaaggaa aggccatcgt tgaagatgcc    660
tctgccgaca gtggtcccaa agatggaccc ccacccacga ggagcatcgt ggaaaaagaa    720
gacgttccaa ccacgtcttc aaagcaagtg gattgatgtg atatctccac tgacgtaagg    780
gatgacgcac aatcccacta tccttcgcaa gaccctttcct ctatataagg aagttcattt    840
catttggaga ggacacacaa tttcagctca agtgtttctt actctctcat ttccatttta    900
gccatgg                                                              907
```

<210> SEQ ID NO 18
<211> LENGTH: 1026
<212> TYPE: PRT
<213> ORGANISM: Oryza sativa

<400> SEQUENCE: 18

```
Met Ile Ser Leu Pro Leu Leu Phe Val Leu Leu Phe Ser Ala Leu
 1               5                  10                  15

Leu Leu Cys Pro Ser Ser Asp Asp Gly Asp Ala Ala Gly Asp
            20                  25                  30

Glu Leu Ala Leu Leu Ser Phe Lys Ser Ser Leu Tyr Gln Gly Gly
        35                  40                  45

Gln Ser Leu Ala Ser Trp Asn Thr Ser Gly His Gly Gln His Cys Thr
    50                  55                  60

Trp Val Gly Val Val Cys Gly Arg Arg Arg Arg His Pro His Arg
 65              70                  75                  80

Val Val Lys Leu Leu Leu Arg Ser Ser Asn Leu Ser Gly Ile Ile Ser
                85                  90                  95

Pro Ser Leu Gly Asn Leu Ser Phe Leu Arg Glu Leu Asp Leu Gly Asp
            100                 105                 110

Asn Tyr Leu Ser Gly Glu Ile Pro Pro Glu Leu Ser Arg Leu Ser Arg
        115                 120                 125

Leu Gln Leu Leu Glu Leu Ser Asp Asn Ser Ile Gln Gly Ser Ile Pro
    130                 135                 140

Ala Ala Ile Gly Ala Cys Thr Lys Leu Thr Ser Leu Asp Leu Ser His
145                 150                 155                 160

Asn Gln Leu Arg Gly Met Ile Pro Arg Glu Ile Gly Ala Ser Leu Lys
                165                 170                 175

His Leu Ser Asn Leu Tyr Leu Tyr Lys Asn Gly Leu Ser Gly Glu Ile
            180                 185                 190

Pro Ser Ala Leu Gly Asn Leu Thr Ser Leu Gln Glu Phe Asp Leu Ser
        195                 200                 205

Phe Asn Arg Leu Ser Gly Ala Ile Pro Ser Ser Leu Gly Gln Leu Ser
    210                 215                 220

Ser Leu Leu Thr Met Asn Leu Gly Gln Asn Asn Leu Ser Gly Met Ile
225                 230                 235                 240

Pro Asn Ser Ile Trp Asn Leu Ser Ser Leu Arg Ala Phe Ser Val Arg
```

-continued

```
                245                 250                 255
Glu Asn Lys Leu Gly Gly Met Ile Pro Thr Asn Ala Phe Lys Thr Leu
            260                 265                 270
His Leu Leu Glu Val Ile Asp Met Gly Thr Asn Arg Phe His Gly Lys
            275                 280                 285
Ile Pro Ala Ser Val Ala Asn Ala Ser His Leu Thr Val Ile Gln Ile
            290                 295                 300
Tyr Gly Asn Leu Phe Ser Gly Ile Ile Thr Ser Gly Phe Gly Arg Leu
305                 310                 315                 320
Arg Asn Leu Thr Glu Leu Tyr Leu Trp Arg Asn Leu Phe Gln Thr Arg
            325                 330                 335
Glu Gln Asp Asp Trp Gly Phe Ile Ser Asp Leu Thr Asn Cys Ser Lys
            340                 345                 350
Leu Gln Thr Leu Asn Leu Gly Glu Asn Asn Leu Gly Gly Val Leu Pro
            355                 360                 365
Asn Ser Phe Ser Asn Leu Ser Thr Ser Leu Ser Phe Leu Ala Leu Glu
            370                 375                 380
Leu Asn Lys Ile Thr Gly Ser Ile Pro Lys Asp Ile Gly Asn Leu Ile
385                 390                 395                 400
Gly Leu Gln His Leu Tyr Leu Cys Asn Asn Asn Phe Arg Gly Ser Leu
                405                 410                 415
Pro Ser Ser Leu Gly Arg Leu Lys Asn Leu Gly Ile Leu Leu Ala Tyr
                420                 425                 430
Glu Asn Asn Leu Ser Gly Ser Ile Pro Leu Ala Ile Gly Asn Leu Thr
                435                 440                 445
Glu Leu Asn Ile Leu Leu Leu Gly Thr Asn Lys Phe Ser Gly Trp Ile
450                 455                 460
Pro Tyr Thr Leu Ser Asn Leu Thr Asn Leu Leu Ser Leu Gly Leu Ser
465                 470                 475                 480
Thr Asn Asn Leu Ser Gly Pro Ile Pro Ser Glu Leu Phe Asn Ile Gln
                485                 490                 495
Thr Leu Ser Ile Met Ile Asn Val Ser Lys Asn Asn Leu Glu Gly Ser
                500                 505                 510
Ile Pro Gln Glu Ile Gly His Leu Lys Asn Leu Val Glu Phe His Ala
                515                 520                 525
Glu Ser Asn Arg Leu Ser Gly Lys Ile Pro Asn Thr Leu Gly Asp Cys
            530                 535                 540
Gln Leu Leu Arg Tyr Leu Tyr Leu Gln Asn Asn Leu Leu Ser Gly Ser
545                 550                 555                 560
Ile Pro Ser Ala Leu Gly Gln Leu Lys Gly Leu Glu Thr Leu Asp Leu
                565                 570                 575
Ser Ser Asn Asn Leu Ser Gly Gln Ile Pro Thr Ser Leu Ala Asp Ile
            580                 585                 590
Thr Met Leu His Ser Leu Asn Leu Ser Phe Asn Ser Phe Val Gly Glu
            595                 600                 605
Val Pro Thr Ile Gly Ala Phe Ala Ala Ala Ser Gly Ile Ser Ile Gln
        610                 615                 620
Gly Asn Ala Lys Leu Cys Gly Gly Ile Pro Asp Leu His Leu Pro Arg
625                 630                 635                 640
Cys Cys Pro Leu Leu Glu Asn Arg Lys His Phe Pro Val Leu Pro Ile
                645                 650                 655
Ser Val Ser Leu Ala Ala Ala Leu Ala Ile Leu Ser Ser Leu Tyr Leu
                660                 665                 670
```

-continued

```
Leu Ile Thr Trp His Lys Arg Thr Lys Gly Ala Pro Ser Arg Thr
            675                 680                 685

Ser Met Lys Gly His Pro Leu Val Ser Tyr Ser Gln Leu Val Lys Ala
        690                 695                 700

Thr Asp Gly Phe Ala Pro Thr Asn Leu Leu Gly Ser Gly Ser Phe Gly
705                 710                 715                 720

Ser Val Tyr Lys Gly Lys Leu Asn Ile Gln Asp His Val Ala Val Lys
                725                 730                 735

Val Leu Lys Leu Glu Asn Pro Lys Ala Leu Lys Ser Phe Thr Ala Glu
            740                 745                 750

Cys Glu Ala Leu Arg Asn Met Arg His Arg Asn Leu Val Lys Ile Val
            755                 760                 765

Thr Ile Cys Ser Ser Ile Asp Asn Arg Gly Asn Asp Phe Lys Ala Ile
        770                 775                 780

Val Tyr Asp Phe Met Pro Asn Gly Ser Leu Glu Asp Trp Ile His Pro
785                 790                 795                 800

Glu Thr Asn Asp Gln Ala Asp Gln Arg His Leu Asn Leu His Arg Arg
                805                 810                 815

Val Thr Ile Leu Leu Asp Val Ala Cys Ala Leu Asp Tyr Leu His Arg
            820                 825                 830

His Gly Pro Glu Pro Val Val His Cys Asp Ile Lys Ser Ser Asn Val
            835                 840                 845

Leu Leu Asp Ser Asp Met Val Ala His Val Gly Asp Phe Gly Leu Ala
        850                 855                 860

Arg Ile Leu Val Asp Gly Thr Ser Leu Ile Gln Gln Ser Thr Ser Ser
865                 870                 875                 880

Met Gly Phe Ile Gly Thr Ile Gly Tyr Ala Ala Pro Glu Tyr Gly Val
                885                 890                 895

Gly Leu Ile Ala Ser Thr His Gly Asp Ile Tyr Ser Tyr Gly Ile Leu
            900                 905                 910

Val Leu Glu Ile Val Thr Gly Lys Arg Pro Thr Asp Ser Thr Phe Arg
            915                 920                 925

Pro Asp Leu Gly Leu Arg Gln Tyr Val Glu Leu Gly Leu His Gly Arg
930                 935                 940

Val Thr Asp Val Val Asp Thr Lys Leu Ile Leu Asp Ser Glu Asn Trp
945                 950                 955                 960

Leu Asn Ser Thr Asn Asn Ser Pro Cys Arg Arg Ile Thr Glu Cys Ile
                965                 970                 975

Val Trp Leu Leu Arg Leu Gly Leu Ser Cys Ser Gln Glu Leu Pro Ser
            980                 985                 990

Ser Arg Thr Pro Thr Gly Asp Ile Ile Asp Glu Leu Asn Ala Ile Lys
            995                 1000                1005

Gln Asn Leu Ser Gly Leu Phe Pro Val Cys Glu Gly Gly Ser Leu Glu
    1010                1015                1020

Phe Glx
1025
```

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 19
ccggtacctc atgatatcac tcccattatt gc                32

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 20
ggagatcttc agaattcaag gctcccacc                29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 21
ccttcaagaa ctttcatgaa aggccaccc                29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 22
ctcccggatc ctcacactgg aaacaatcc                29

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 23
caattatcat gagatttgtt ctcttttc                28

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 24
ggcagatgta gatcggcacg gcaagagtg                29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 25
cactcttgcc gtgccgatct acatctgcc                29

<210> SEQ ID NO 26
<211> LENGTH: 30
<212> TYPE: PRT

<213> ORGANISM: Artificial Sequence
<220> FEATURE:
<223> OTHER INFORMATION: Description of Artificial Sequence:PR-1a signal
      peptide from Nicotiana tabacum

<400> SEQUENCE: 26

Met Gly Phe Val Leu Phe Ser Gln Leu Pro Ser Phe Leu Leu Val Ser
 1               5                  10                  15

Thr Leu Leu Leu Phe Leu Val Ile Ser His Ser Cys Arg Ala
                20                  25                  30

<210> SEQ ID NO 27
<211> LENGTH: 2704
<212> TYPE: DNA
<213> ORGANISM: Artificial Sequence: pUC 28 high copy cloning vector
<220> FEATURE:
<223> OTHER INFORMATION: Description of Artificial Sequence:
      Polynucleotide

<400> SEQUENCE: 27

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccaa | gcttgcatgc | ctgcaggtcg | 420 |
| actctagagg | atccccgggt | accgagctca | tcgatccatg | gagatctgaa | ttcgtaatca | 480 |
| tggtcatagc | tgtttcctgt | gtgaaattgt | tatccgctca | caattccaca | caacatacga | 540 |
| gccggaagca | taaagtgtaa | agcctgggt | gcctaatgag | tgagctaact | cacattaatt | 600 |
| gcgttgcgct | cactgcccgc | tttccagtcg | ggaaacctgt | cgtgccagct | gcattaatga | 660 |
| atcggccaac | gcgcggggag | aggcggtttg | cgtattgggc | gctcttccgc | ttcctcgctc | 720 |
| actgactcgc | tgcgctcggt | cgttcggctg | cggcgagcgg | tatcagctca | ctcaaaggcg | 780 |
| gtaatacggt | tatccacaga | atcaggggat | aacgcaggaa | agaacatgtg | agcaaaaggc | 840 |
| cagcaaaagg | ccaggaaccg | taaaaaggcc | gcgttgctgg | cgttttttcca | taggctccgc | 900 |
| cccctgacg | agcatcacaa | aaatcgacgc | tcaagtcaga | ggtggcgaaa | cccgacagga | 960 |
| ctataaagat | accaggcgtt | tcccctgga | agctccctcg | tgcgctctcc | tgttccgacc | 1020 |
| ctgccgctta | ccggatacct | gtccgccttt | ctcccttcgg | gaagcgtggc | gctttctcaa | 1080 |
| tgctcacgct | gtaggtatct | cagttcggtg | taggtcgttc | gctccaagct | gggctgtgtg | 1140 |
| cacgaaccc | ccgttcagcc | cgaccgctgc | gccttatccg | gtaactatcg | tcttgagtcc | 1200 |
| aacccggtaa | gacacgactt | atcgccactg | gcagcagcca | ctggtaacag | gattagcaga | 1260 |
| gcgaggtatg | taggcggtgc | tacagagttc | ttgaagtggt | ggcctaacta | cggctacact | 1320 |
| agaaggacag | tatttggtat | ctgcgctctg | ctgaagccag | ttaccttcgg | aaaaagagtt | 1380 |
| ggtagctctt | gatccggcaa | acaaaccacc | gctggtagcg | gtggtttttt | tgtttgcaag | 1440 |
| cagcagatta | cgcgcagaaa | aaaaggatct | caagaagatc | ctttgatctt | ttctacgggg | 1500 |
| tctgacgctc | agtggaacga | aaactcacgt | taagggattt | tggtcatgag | attatcaaaa | 1560 |
| aggatcttca | cctagatcct | ttaaattaa | aaatgaagtt | ttaaatcaat | ctaaagtata | 1620 |
| tatgagtaaa | cttggtctga | cagttaccaa | tgcttaatca | gtgaggcacc | tatctcagcg | 1680 |

-continued

| | |
|---|---|
| atctgtctat ttcgttcatc catagttgcc tgactccccg tcgtgtagat aactacgata | 1740 |
| cgggagggct taccatctgg ccccagtgct gcaatgatac cgcgagaccc acgctcaccg | 1800 |
| gctccagatt tatcagcaat aaaccagcca gccggaaggg ccgagcgcag aagtggtcct | 1860 |
| gcaactttat ccgcctccat ccagtctatt aattgttgcc gggaagctag agtaagtagt | 1920 |
| tcgccagtta atagtttgcg caacgttgtt gccattgcta caggcatcgt ggtgtcacgc | 1980 |
| tcgtcgtttg gtatggcttc attcagctcc ggttcccaac gatcaaggcg agttacatga | 2040 |
| tcccccatgt tgtgcaaaaa agcggttagc tccttcggtc ctccgatcgt tgtcagaagt | 2100 |
| aagttggccg cagtgttatc actcatggtt atggcagcac tgcataattc tcttactgtc | 2160 |
| atgccatccg taagatgctt ttctgtgact ggtgagtact caaccaagtc attctgagaa | 2220 |
| tagtgtatgc ggcgaccgag ttgctcttgc ccggcgtcaa tacgggataa taccgcgcca | 2280 |
| catagcagaa cttttaaaagt gctcatcatt ggaaaacgtt cttcggggcg aaaactctca | 2340 |
| aggatcttac cgctgttgag atccagttcg atgtaaccca ctcgtgcacc caactgatct | 2400 |
| tcagcatctt ttactttcac cagcgtttct gggtgagcaa aaacaggaag gcaaaatgcc | 2460 |
| gcaaaaaagg gaataagggc gacacggaaa tgttgaatac tcatactctt ccttttttcaa | 2520 |
| tattattgaa gcatttatca gggttattgt ctcatgagcg gatacatatt tgaatgtatt | 2580 |
| tagaaaaata aacaaatagg ggttccgcgc acatttcccc gaaaagtgcc acctgacgtc | 2640 |
| taagaaacca ttattatcat gacattaacc tataaaaata ggcgtatcac gaggcccttt | 2700 |
| cgtc | 2704 |

<210> SEQ ID NO 28
<211> LENGTH: 3078
<212> TYPE: DNA
<213> ORGANISM: Oryza sativa

<400> SEQUENCE: 28

| | |
|---|---|
| atgatatcac tcccattatt gctcttcgtc ctgttgttct ctgcgctgct gctctgccct | 60 |
| tcaagcagtg acgacgatgg tgatgctgcc ggcgacgaac tcgcgctgct ctcttttcaag | 120 |
| tcatccctgc tataccaggg gggccagtcg ctggcatctt ggaacacgtc cggccacggc | 180 |
| cagcactgca catgggtggg tgttgtgtgc ggccgccgcc gccgccggca cccacacagg | 240 |
| gtggtgaagc tgctgctgcg ctcctccaac ctgtccggga tcatctcgcc gtcgctcggc | 300 |
| aacctgtcct tcctcaggga gctggacctc ggcgacaact acctctccgg cgagatacca | 360 |
| ccggagctca gccgtctcag caggcttcag ctgctggagc tgagcgataa ctccatccaa | 420 |
| gggagcatcc ccgcggccat ggagcatgcc accaagttga catcgctaga cctcagccac | 480 |
| aaccaactgc gaggtatgat cccacgtgag attggtgcca gcttgaaaca tctctcgaat | 540 |
| ttgtaccttt acaaaaatgg tttgtcagga gagattccat ccgctttggg caatctcact | 600 |
| agcctccagg agtttgattt gagcttcaac agattatcag gagctatacc ttcatcactg | 660 |
| gggcagctca gcagtctatt gactatgaat ttgggacaga acaatctaag tgggatgatc | 720 |
| cccaattcta tctggaacct ttcgtctcta agagcgttta gtgtcagaga aacaagcta | 780 |
| ggtggtatga tccctacaaa tgcattcaaa acccttcacc tcctcgaggt gatagatatg | 840 |
| ggcactaacc gtttccatgg caaaatccct gcctcagttg ctaatgcttc tcatttgaca | 900 |
| gtgattcaga tttatggcaa cttgttcagt ggaattatca cctcgggggtt tggaaggtta | 960 |
| agaaatctca cagaactgta tctctggaga aatttgtttc aaactagaga acaagatgat | 1020 |

-continued

```
tgggggttca tttctgacct aacaaattgc tccaaattac aaacattgaa cttgggagaa    1080
aataacctgg ggggagttct tcctaattcg ttttccaatc tttccacttc gcttagtttt    1140
cttgcacttg aattgaataa gatcacagga agcattccga aggatattgg caatcttatt    1200
ggcttacaac atctctatct ctgcaacaac aatttcagag ggtctcttcc atcatcgttg    1260
ggcaggctta aaaacttagg cattctactc gcctacgaaa acaacttgag cggttcgatc    1320
ccgttggcca taggaaatct tactgaactt aatatcttac tgctcggcac caacaaattc    1380
agtggttgga taccatacac actctcaaac ctcacaaact tgttgtcatt aggcctttca    1440
actaataacc ttagtggtcc aatacccagt gaattattca atattcaaac actatcaata    1500
atgatcaatg tatcaaaaaa taacttggag ggatcaatac cacaagaaat agggcatctc    1560
aaaaatctag tagaatttca tgcagaatcg aatagattat caggtaaaat ccctaacacg    1620
cttggtgatt gccagctctt acggtatctt tatctgcaaa ataatttgtt atctggtagc    1680
atcccatcag ccttgggtca gctgaaaggt ctcgaaactc ttgatctctc aagcaacaat    1740
ttgtcaggcc agatacccac atccttagca gatattacta tgcttcattc cttgaacctt    1800
tctttcaaca gctttgtggg ggaagtgcca accattggtg cttttcgcagc tgcatccggg    1860 atctcaatcc aaggcaatgc caaactctgt ggtggaatac ctgatctaca tctgcctcga    1920
tgttgtccat tactagagaa cagaaaacat ttcccagttc tacctatttc tgtttctctg    1980
gccgcagcac tggccatcct ctcatcactc tacttgctta taacctggca aagagaact     2040 aaaaagggag ccccttcaag aacttccatg aaaggccacc cattggtctc ttattcgcag    2100
ttggtaaaag caacagatgg tttcgcgccg accaatttgt tgggttctgg atcatttggc    2160
tcagtataca aaggaaagct taatatccaa gatcatgttg cagtgaaggt actaaagctt    2220
gaaaatccta aggcgctcaa gagtttcact gccgaatgtg aagcactacg aaatatgcga    2280
catcgaaatc ttgtcaagat agttacaatt gctcgagca ttgataacag agggaacgat     2340
ttcaaagcaa ttgtgtatga cttcatgccc aacggcagtc tggaagattg gatacaccct    2400
gaaacaaatg atcaagcaga ccagaggcac ttgaatctgc atcgaagagt gaccatacta    2460
cttgatgttg cctgcgcact ggactatctt caccgccatg gccctgaacc tgttgtacac    2520
tgtgatatta aatcaagcaa tgtgctgtta gattctgata tggtagccca tgttggagat    2580
tttgggcttg caagaatact tgttgatggg acctcattga tacaacagtc aacaagctcg    2640
atgggattta tagggacaat tggctatgca gcaccagagt atggcgttgg gctcattgca    2700
tcaacgcatg gagatatttta cagctatgga attctagtgc tggaaatagt aaccgggaag    2760
cggccaactg acagtacatt cagacccgat ttgggcctcc gtcagtacgt tgaactgggc    2820
ctacatggca gagtgacgga tgttgttgac acgaagctca ttttggattc tgagaactgg    2880
ctgaacagta caaataattc tccatgtaga agaatcactg aatgcattgt ttggctgctt    2940
agacttgggt tgtcttgctc tcaggaattg ccatcgagta gaacgccaac cggagatatc    3000
atcgacgaac tgaatgccat caaacagaat ctctccggat tgtttccagt gtgtgaaggt    3060
gggagccttg aattctga                                                  3078
```

<210> SEQ ID NO 29
<211> LENGTH: 90
<212> TYPE: DNA
<213> ORGANISM: Artificial Sequence
<220> FEATURE:
<223> OTHER INFORMATION: Description of Artificial Sequence:PR 1a signal
      peptide from Nicotiana tabacum

```
<400> SEQUENCE: 29
atgggatttg ttctcttttc acaattgcct tcatttcttc ttgtctctac acttctctta        60
ttcctagtaa tatcccactc ttgccgtgcc                                          90
```